(12) United States Patent
Cass et al.

(10) Patent No.: US 6,312,906 B1
(45) Date of Patent: Nov. 6, 2001

(54) IMMOBILIZED NUCLEIC ACID HYBRIDIZATION REAGENT AND METHOD

(75) Inventors: Anthony Cass; Christophe Valat, both of London (GB); Adam Steel, Silver Spring, MD (US)

(73) Assignees: Imperial College Innovations, Ltd., London (GB); Gene Logic, Inc., Gaithersburg, MD (US)

( * ) Notice: Subject to any disclaimer, the term of this patent is extended or adjusted under 35 U.S.C. 154(b) by 0 days.

(21) Appl. No.: 09/482,607

(22) Filed: Jan. 14, 2000

Related U.S. Application Data

(60) Provisional application No. 60/116,063, filed on Jan. 15, 1999.

(51) Int. Cl.[7] .............................. C12Q 1/68; C12M 1/34; C07H 21/04
(52) U.S. Cl. ........................ 435/6; 435/287.2; 536/24.3
(58) Field of Search ................... 435/6, 287.2; 536/24.3

(56) References Cited

U.S. PATENT DOCUMENTS

| | | | |
|---|---|---|---|
| 5,035,863 | 7/1991 | Finlan et al. | 422/82.05 |
| 5,143,854 | 9/1992 | Pirrung et al. | 436/518 |
| 5,332,659 | 7/1994 | Kidwell | 435/6 |
| 5,571,388 | 11/1996 | Patonay et al. | 204/461 |
| 5,741,644 | 4/1998 | Kambara et al. | 435/6 |
| 5,800,995 | 9/1998 | Patonay et al. | 435/6 |
| 5,824,473 | 10/1998 | Meade et al. | 435/6 |
| 5,843,767 | 12/1998 | Beattie | 435/287.1 |
| 6,037,130 * | 2/2000 | Tyagi et al. | 435/6 |

FOREIGN PATENT DOCUMENTS

| | | |
|---|---|---|
| 0 745 690 | 4/1996 | (EP) . |
| 0 721 016 | 10/1996 | (EP) . |
| 0 881 302 | 2/1998 | (EP) . |
| 93/15406 | 8/1993 | (WO) . |
| 97/31256 | 8/1997 | (WO) . |
| 97/39008 | 10/1997 | (WO) . |

OTHER PUBLICATIONS

Tyage et al., "Molecular Beacons: Probes That Fluoresce Upon Hybrization", *Research Article*, Nature Biotechnology vol. 14 pp. 303–308, 1996.

Gruber et al., "Biotin–Fluorophore Conjugates With Poly-(ethylene glycol) Spacers Retain Intense Fluorescence After Binding To Avidin And Streptavidiin", *Bioconjugate Chen.*, vol. 8:552–559, (1997).

Tian et al., "Fluorescence Quenching Of Cyanine Dyes Adsorbed Onto The Surface Of Colloid Semiconductors", *Journal Of Photographic Science*, vol. 40(4):100–104, (1992).

Wennmalm et al., "Conformational Fluctuations In Single DNA Molecules", *Proc. Natl. Acad. Sci. USA*, vol. 94:10641–10646, (1997).

(List continued on next page.)

*Primary Examiner*—Robert A. Schwartzman
*Assistant Examiner*—Katharine F. Davis
(74) *Attorney, Agent, or Firm*—Foley & Lardner

(57) ABSTRACT

A fluorescently labeled nucleic acid having a hairpin structure between the fluorophore label and a point of attachment to a solid phase is useful as a probe to detect nucleic acid from a sample. The solid phase quenches the fluorophore label when the hairpin structure exists but this quenching is relieved by duplex formation between probe and a sample oligonucleotide. Probes for specific nucleic acid sequences can be immobilized as arrays on solid phase surfaces for detection of multiple nucleic acid sequences simultaneously from electrophoresis gels and from aqueous solutions. These probes and methods for their use can be combined with known solid phases, particularly those used for plasmon surface detection and electron transfer detection of nucleic acid. The probes can be washed and reused, and have other advantageous features over known probe methods.

28 Claims, 4 Drawing Sheets

OTHER PUBLICATIONS

Abstract, "Peptides, Antibodies, and FRET On Beads In Flow Cytometry", (09/99) Tione et al. Cytometry 37:21.

Morrison, "Detection Of Energy Transfer And Fluorescence Quenching", pp. 311–353, (1992) Chapter 13 Nonisotopic DNA Probe Techniques Academic Press editor Larry Kricka.

Nikiforov et al., "Genetic Bit Analysis: A Solid Phase Method For Typing Single Nucleotide Polymorphisms", *Nulcleic Acids Research*, vol. 22(1):4167–4175, (1994).

Yershov et al., "DNA Analysis And Diagnostics On Oligonucleotide Microchips", *Proc. Natl. Acad. Sci. USA*, vol. 93:4913–4918, (1996).

Ju et al., "Fluorescence Energy Transfer Dye–Labeled Primers For DNA Sequencing And Analysis", *Proc. Natl. Acad. Sci. USA*, vol. 92:4347–4351, (1995).

Nelson et al., "Oligonucleotide Labeling Methods 3. Direct Labeling Of Oligonucleotides Employing A Novel, Non –Nucleosidic, 2–Aminobutyl–1,3–propanediol Backbone", *Nucleic Acids Research*, vol. 20(23):6253–6259, (1992).

Kwok et al., "Comparative Analysis Of Human DNA Variations By Fluorescence–Based Sequencing Of PCR Products", *Genomics*, vol. 23:138–144, (1994).

Parham et al., "Carboxyl–Terminal Sequential Degradation", *Biochemical and Biophysical Research Communications*, vol. 80(1):1–6, (1978).

Lund et al., "Assessment Of Methods For Covalent Binding Of Nucleic Acids To Magnetic Beads, Dynabeads And The Characteristics Of The Bound Nulcleic Acids In Hybridization Reactions", *Nucleic Acids Research*, vol. 16(22):10861–10881, (1988).

Lee et al., "Heterogeneous Catalysis On Platinum And Self–Assembled Monolayers On Metal And Metal Oxide Surfaces (Note a)", *Pure & Appl. Chem.*, vol. 63(6):821–828, (1991).

Wodicka et al., "Genome–Wide Expression Monitoring In Saccharomyces Cerevisiae", *Nature Biotechnology*, vol. 15:1359–1367, (1997).

Fodor et al., "Light–Directed, Spatially Addressable Parallel Chemical Synthesis", *Science*, vol. 251:767–773, (1991).

Cho et al., "Parallel Analysis Of Genetic Selections Using Whole Genome Oligonucleotide Arrays", *Proc. Natl. Acad. Sci, USA*, vol. 954:3752–3757, (1998).

Lockhart et al., "Expression Monitoring By Hybridization To High–Density Oligonucleotide Arrays", *Nature Biotechnology*, vol. 14:1675–1680, (1996).

Milner et al., "Selecting Effective Antisense Reagents On Combinatorial Oligonucleotide Arrays". *Nature Biotechnology*, vol. 15:537–541, (1997).

Pease et al., "Light–Generated Oligonucleotide Arrays For Rapid DNA Sequence Analysis", *Pro. Natl. Acad. Sci. USA*, vol. 91:5022–5026, (1994).

* cited by examiner

Oligonucleotide Adapted Fluorophore-quencher surface:

IMMOBILIZED NUCLEIC ACID HYBRIDIZATION REAGENT AND METHOD

This application claims priority to U.S. Ser. No. 60/116,063 filed on Jan. 15, 1999, and which is incorporated in its entirety by reference.

FIELD OF THE INVENTION

The invention relates to fluorescent nucleic acid probes having a fluorescent reporter moiety for detection of nucleic acid. More specifically, the invention relates to fluorescent probes that are useful for solid phase based hybridization assays and to methods of nucleic acid detection on solid surfaces.

BACKGROUND OF THE INVENTION

Sequence-specific hybridization of oligonucleotide probes is a useful and very valuable reaction for detecting and identifying a specific polynucleotide sequence. This identification of a specific oligonucleotide sequence requires a readout system that produces a signal indicating hybridization of the specific target sequence to an oligonucleotide probe. A popular readout system is fluorescent labeling of a DNA probe, which creates a fluorescent signal in response to a specific hybridization reaction. Fluorescence labeled probes and sequence-specific methods of their use generally employ a soluble water phase nucleic acid that is labeled with a reporter moiety such as a fluorescent label, to facilitate detection of probe hybridization. Some of these methods employ fluorescence energy transfer ("FRET") to detect probe hybridization rather than direct detection of fluorescence intensity.

In the FRET technique a light source illuminates the sample. Energy of an absorbed photon from the light source can transfer from a donor fluorophore to an acceptor dye (which may or may not be a fluorophore) when (i) the absorption spectrum of the acceptor dye overlaps the emission spectrum of the excited fluorophore and (ii) the two molecules are in close proximity. The excited-state energy of the donor fluorophore transfers to the neighboring acceptor by the phenomenon of resonance dipole-induced dipole interaction, thereby causing quenching of the donor fluorescence. Alternatively, if the acceptor also is a fluorophore, the intensity of its fluorescence may be enhanced. The efficiency of energy transfer is highly dependent on the distance between the donor and acceptor, and equations predicting these relationships have been developed by Forster (*Ann. Phys.* 2:55–75 (1948)). The distance between donor and acceptor dyes at which energy transfer efficiency is 50% is referred to as the Forster distance (R[o]). Other mechanisms of fluorescence quenching also are known including, for example, charge transfer and collisional quenching.

The FRET technique is particularly useful for detecting hybridization of nucleic acid because of a marked change in the fluorescence properties of donor fluor and/or acceptor dye label when they are brought in close physical proximity by the hybridization of two complementary oligonucleotides. In this format, this change in fluorescence may be measured as a change in the amount of energy transfer or as a change in the amount of fluorescence quenching, and typically is indicated as an increase in the fluorescence intensity of one of the dyes. Thus, the FRET technique potentially can distinguish between unhybridized and hybridized oligonucleotide species without the need to physically separate the species.

Simple FRET systems rely on hybridization between two separate complementary oligonucleotides, one labeled with the donor fluorophore and one labeled with the acceptor. When hybridization occurs, leading to a double-stranded oligonucleotide, quenching and/or increased energy transfer leads to a decrease in donor fluorescence as compared to the fluorescence from the individual single-stranded oligonucleotides. Several formats for FRET hybridization assays are reviewed in *Nonisotopic DNA Probe Techniques* (1992. Academic Press, Inc., pgs. 311–352) and in WO 97/22719.

Alternatively, the donor and acceptor may be linked to a single oligonucleotide and used to monitor a change between a hairpin conformation and a non-hairpin conformation of the oligonucleotide. In this format, donor fluorescence decreases when an internal hairpin structure is formed and increases when the hairpin dissociates, for example when a complementary region of the oligonucleotide hybridizes with a separate oligomer instead of itself. For example, a partially self-complementary oligonucleotide may be dye-labeled at both ends and may form a hairpin between the ends, bringing the two dyes into close proximity and permitting energy transfer and quenching between the dyes. Hybridization of an internal region of the oligomer with a second nucleic acid disrupts the hairpin and increases the distance between the two dyes, thus reducing quenching, and allowing fluorescent dyes to emit photons upon their excitation.

The FRET technique has been used to detect a change of a hairpin structure in solution as described by U.S. Pat. No. 5,332,659, issued Jul. 26, 1994 and by WO 97/22719, published Jun. 26, 1997. The FRET technique disclosed in those publications does not require a separation step to measure hybridization and furthermore can use reagents that are more stable than alternative reagents such as radioisotopic or enzyme labeled probes. Unfortunately, the disclosed FRET techniques cannot be used to simultaneously observe hybridization events of multiple targets, particularly when the target molecules are present in the same solution. This is a serious deficiency for modern genetic analyses which require the ability to use multiple DNA probes to determine the presence of multiple sequences in a single sample.

Another problem in the art is that a fluorescently labeled nucleic acid reagent, such as those described above, cannot easily be reused. Yet another problem is that the labeled nucleic acid must contain a second dye that quenches the first. Dyes typically are hydrophobic, which leads to self-association in aqueous solution, with consequent steric hindrance of base pair formation. Such steric hindrance is a significant barrier to duplex formation when the oligonucleotide is small and the two dyes have a correspondingly larger steric effect.

Yet another problem is that the solution methods use a detection system that relies on a difference in wavelength of emission (U.S. Pat. No. 5,332,659) or intensity (WO 97/22719, WO 97/39008) that is superimposed on a much higher light emission background. The high light emission background significantly limits detection sensitivity. Furthermore, only a few probes can be used and even these suffer great loss of sensitivity because the excitation and emission light from one probe species contributes to the background when measuring another species. Accordingly, a great need exists for an assay device and method that can take advantage of the sensitivity of fluorescence detection but which does not suffer from the problems described above.

SUMMARY OF THE INVENTION

It is therefore an object of the invention to provide improved methods for detecting nucleic acid in biological samples. It is another object of the invention to provide tools, methods and materials for simultaneous assay of multiple nucleic acid species from the same sample.

In accomplishing these objects, there has been provided, in accordance with one aspect of the invention, a method for detecting the presence of a nucleic acid in a test sample, comprising: providing a solid phase having an oligonucleotide bound thereon where the oligonucleotide comprises a fluorophore. The fluorophore is covalendy attached to one end of the oligonucleotide and the solid phase is linked to the opposite end of the oligonucleotide, and the oligonucleotide further comprises at least one hairpin structure between the two ends. The test sample is incubated with the solid phase under conditions suitable for complementary binding between the oligonucleotide and nucleic acid from the test sample; and the presence of the target molecule is indicated by detecting fluorescence from the fluorophore. The oligonucleotide probe may be directly covalently bound to said solid phase, or indirectly linked to said solid phase. For example, the oligonucleotide may be indirectly linked by hybridization to a nucleic acid that is immobilized on said solid phase. The nucleic acid may comprise a quenching moiety. The solid phase may comprise an array of discrete regions wherein each region contains a nucleic acid comprising a quenching moiety. The array may contain a plurality of different nucleic acids, with each discrete region containing a single nucleic acid.

In another embodiment the invention provides a method for detecting the presence of two or more nucleic acids in a test sample, comprising: providing a solid phase to which two or more oligonucleotides are bound at separate regions, each oligonucleotide comprising a fluorophore. The fluorophore is covalently attached to one end of the oligonucleotide and the solid phase is linked to the opposite end of the oligonucleotide, and the oligonucleotide further comprising at least one hairpin structure between the two ends. The test sample is incubated with the solid phase under conditions suitable for complementary binding between the oligonucleotide and nucleic acid from the test sample; and fluorescence is detected from each of the separate regions of the solid phase.

Another embodiment of the invention is an analytical test device for detecting the presence of a nucleic acid in a test sample comprising: a solid phase surface comprising a material that quenches fluorescence; and a self-complementary single stranded oligonucleotide probe linked to the solid phase surface at one of its ends, the probe comprising a fluorophore attached to its other end and a hairpin structure between the two ends.

Yet another embodiment of the invention provides an analytical test device for detecting the presence of two or more nucleic acids in a test sample comprising: a solid phase surface to which two or more oligonucleotides are bound at separate regions, where each oligonucleotide comprises a fluorophore, with the fluorophore being covalently attached to one end of the oligonucleotide and the solid phase being linked to the opposite end of the oligonucleotide, and where each oligonucleotide further comprises a hairpin structure between the two ends.

In yet another embodiment of the invention there is provided a kit for detecting the presence of a nucleic acid in a test sample. The kit comprises a solid phase packaged within a container, together with instructions. An oligonucleotide is bound to the solid phase, where the oligonucleotide comprises a fluorophore, with the fluorophore being covalently attached to one end of the oligonucleotide and the solid phase being linked the opposite end of the oligonucleotide. The oligonucleotide further comprises a hairpin structure between the two ends.

In a further embodiment of the invention there is provided a fluorescence quenching surface to which at least one type of oligonucleotide is bound and where the oligonucleotide comprises a fluorophore, the fluorophore being covalently attached to one end of the oligonucleotide and the solid phase being linked to the opposite end of the oligonucleotide. The oligonucleotide further comprises at least one hairpin structure between the two ends.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Methods are provided that alleviate the above described problems of soluble probe technology by immobilizing a nucleic acid probe onto a quenching surface. The probe comprises two regions that are self complementary and that intramolecularly hybridize in the absence of a target molecule. The probe also contains a fluorescent moiety. When the probe is intramolecularly hybridized, the fluorescent moiety is in close proximity to the quenching surface and the probe fluorescence is quenched. In the presence of a target molecule, hybridization with the target causes dissociation of the self complementary regions of the probe. This increases the distance between the fluorescent moiety and the quenching surface, leading to reduced quenching and a concomitant increase in fluorescence. In other words, the probe fluoresces in the presence of a complementary nucleic acid but has a negligible or low background signal in the absence of such analyte due to quenching of the probe fluorescence by the surface. The quenching from the surface may come about by a variety of mechanisms that include, but are not limited to, inductive resonance quenching by another dye, which generally has been relied on for earlier probe technologies described above. A description of quenching mechanisms can be found in R. LACKOWITZ, PRINCPLES OF FLUORESCENCE SPECTROSCOPY (Plenum Press, 1983).

Figure 1:
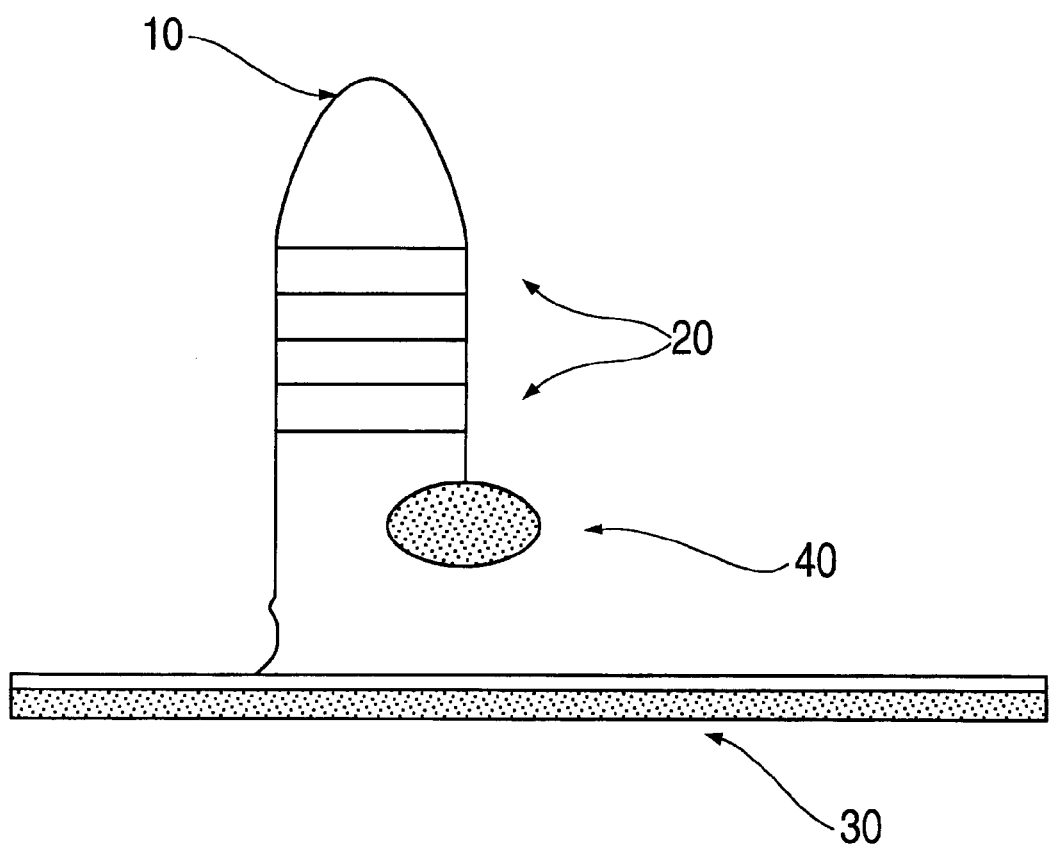
FIG. 1 shows a self-complementary nucleic acid (having a hairpin) on a quenching surface.
Figure 2:
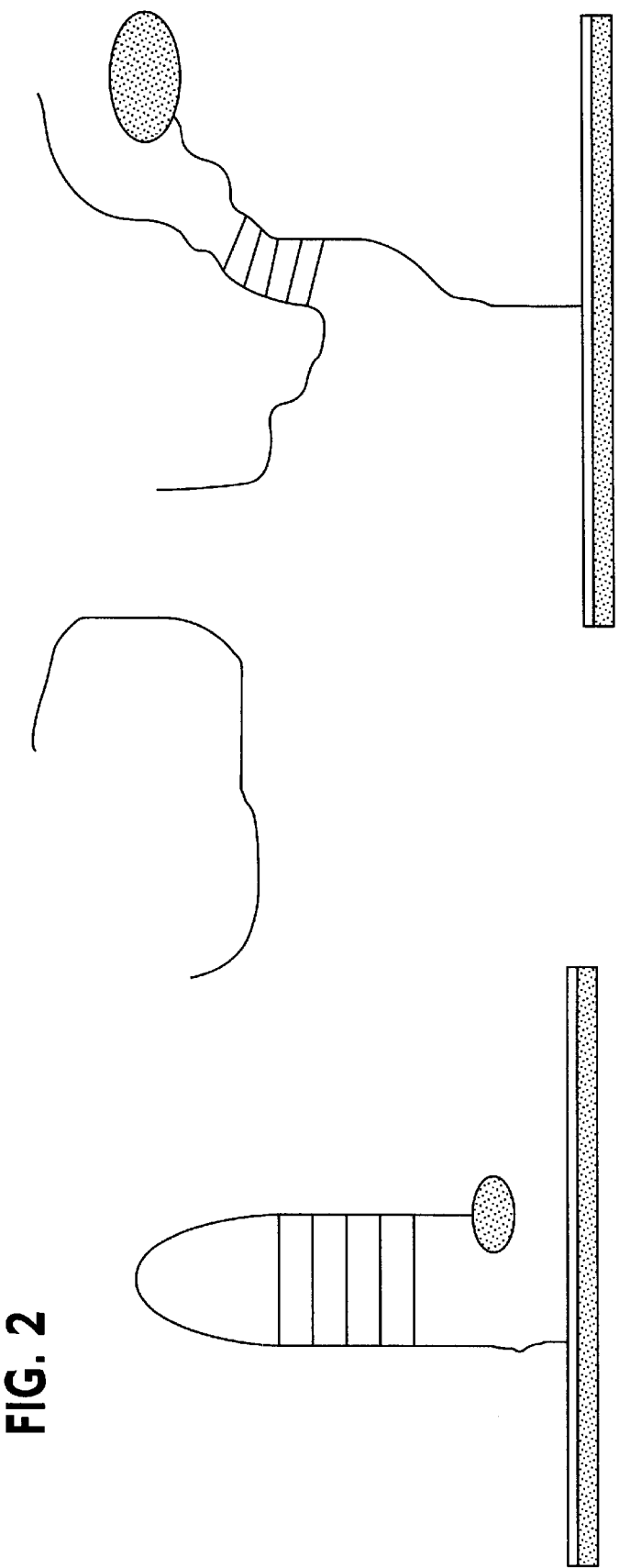
FIG. 2 shows a self-complementary nucleic acid with a disrupted hairpin structure caused by incubation with a target nucleic acid.
Figure 3:
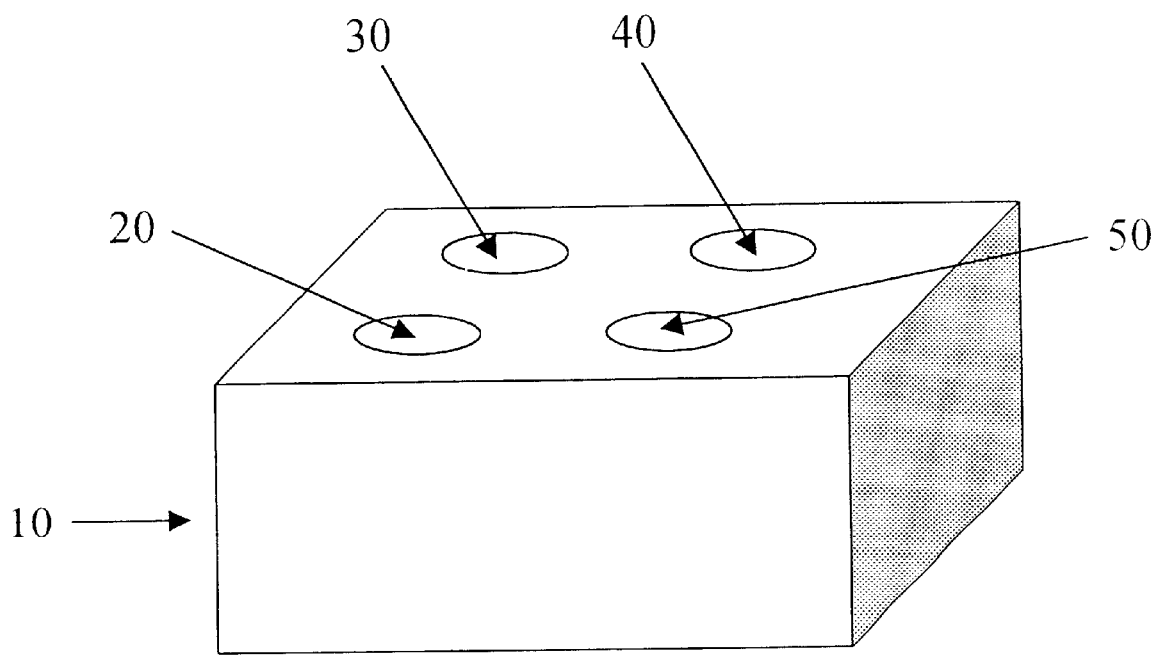
FIG. 3 shows an array of probes (20–50) of the type described in FIG. 1 on a flow through porous form (10). The flow through porous form is suitably manufactured or modified to effect quenching of the fluorophore group of each probe in the hairpin configuration. The probe in each spot (20–50) is complementary to a unique target sequence which hybridizes with the probe resulting in an increase in fluorescence intensity from that region.

As shown in FIG. 1, a probe according to the invention contains at least one internal hairpin loop 10, a portion 20 of which is complementary to the analyte sequence. The nucleic acid is attached at one end to a quenching surface 30 and has a fluorescence tag 40. Unlike the probes disclosed in U.S. Pat. No. 5,332,659, WO 97/22719 and WO 97/39008, in which the probe molecules contain at least two dye molecules, a probe according to the present invention may only have one attached dye (40) and the probe is quenched when it is within a short distance from an immobilizing surface (30). When target nucleic acid analyte is present, the hairpin loop is disrupted and the average distance of the fluorophore from the surface is increased, resulting in enhanced fluorescence emission as illustrated in FIG. 2. Use of a quenching surface in this manner alleviates the disadvantages with the soluble probe technique and provides new opportunities for reusing a probe and using multiple probes simultaneously.

The invention also provides solid phase arrangements of immobilized probes that provide two dimensional devices for simultaneous assay of nucleic acid, and also provides selective readout of individual nucleic acid detection sites in a two-dimensional array.

Further advantages will readily be apparent from a description of specific embodiments as listed below.

A. Immobilized Probes and Techniques

An immobilized probe according to the invention comprises a strand of nucleic acid that has a loop sequence that is complementary to a sequence contained in a target molecule. Such strands are generally known and appreciated in the art as exemplified in the publications described above. FIG. 1 shows an embodiment in which one self-complementary portion of the strand has a fluorophore attached to one end of the oligonucleotide and a second self-complementary portion is linked to a solid phase. The term "fluorophore" as used here means a residue that absorbs light energy and then readmits light energy of a longer wavelength. The residue may be a molecule such as a dye molecule but may also be an atom, such as a europium atom that is phosphorescent under certain conditions, as are known to the skilled artisan. The term "linked to one end of the oligonuc leotide" as used here means that the fluorophore may be at or near (within 40 nucleic acid bases) of the end of a complementary sequence, and more particularly is within 10 nucleic acid bases of the end of the sequence. When a target sequence that is sufficiently complementary to the loop region of the probe is incubated with the probe under appropriate conditions, hybridization with the target can disrupt the probe's internal (self-complementary) base pairing and thus induce the fluorophore to move away from the surface, as shown in FIG. 2

A fluorophore-labeled oligonucleotide can be prepared by a very wide variety of methods that are known in the art. For example, one method is to begin with a polynucleotide primer that is designed to hybridize with the target nucleic acid. In an embodiment useful for genotyping assays where a single nucleotide polymorphism is being detected, the primer binds 3' to the polymorphic site. Each of two dideoxynucleotides representing two possible alleles for the site are labeled with the fluorophore and added to suitable reactions for incorporation into a probe, as describe below.

Two samples of target DNA representing each allele are placed in separate reaction vessels and the initial probe primer is added to each, along with one of the two dideoxynucleotides complementary to the alleles. The two samples are then incubated under suitable conditions in which the polynucleotide hybridizes to the nucleic acid sample in the presence of a thermostable DNA polymerase. The reaction is cycled between thermophilic and mesophilic temperatures under conditions such that the polynucleotide is extended by one base when the dideoxynucleoside triphosphate is complementary to the base on the target DNA responsible for the allele. Such conditions suitable for hybridization and for 3' addition of dideoxynucleoside triphosphates are known (see for example, Sambrook et al., supra; Nikiforov et al, *Nuc Acids Res* 22:4167–4175, 1994; Yershov et al., *Proc Natl Acad Sci* 93:4913–1918, 1996 which are incorporated by reference). The hybridized primers are only extended when the added dideoxynucleotide is complementary to the target DNA at the polymorphic site. The hybridized primers then are denatured to release the fluorophore labeled oligonucleotides to the target.

In a second embodiment, a fluorophore-labeled oligonucleotide is formed by ligation of two polynucleotides, one of which contains the fluorophore and wherein each polynucleotide has a sequence complementary to the target nucleic acid. The ligated polynucleotide has a fluorophore near one end that can be linked to a surface as depicted in FIG. 1 and FIG. 2.

Fluorescent dye-labeled dideoxynucleoside triphosphates and polynucleotide probes can be purchased from commercial sources. Labeled polynucleotides probes can also be prepared by a number of methods. For example, unlabeled polynucleotides can be prepared by excision, transcription or chemical synthesis. Labeling of the polynucleotide probe with a fluorescent dye can be done internally or by end labeling using well known methods (see, for example, Ju et al., *Proc Nat Acad Sci* 92:4347–4351, 1995; Nelson et al. *Nucleic Acids Res* 20:6253–6259, 1992 which are incorporated herein by reference).

The fluorescent-labeled oligonucleotides and polynucleotides of the present invention can hybridize with a sample nucleic acid sequence containing a specific target nucleotide sequence due to complementarity with the target sequence or to a portion of the nucleic acid sequence containing the specific target. Oligomer probes suitable for hybridizing to the nucleic acid preferably contain a minimum of about 6–12 contiguous nucleotides which are substantially complementary to the nucleic acid. The probes preferably are about 15 to about 60 nucleotides in length, more preferably from about 18 to about 40 nucleotides in length, and still more preferably from about 20 to about 30 nucleotides in length. However, where the fluorophore is not positioned immediately at the 5' or 3' end of the synthesized oligonucleotide but, instead, is placed internally, the polynucleotide probe may be substantially longer. For example, the probe may be from about 18 to about 1000 nucleotides long, preferably from 20 to about 200 or more nucleotides, more preferably from about 30 to about 100 nucleotides and yet more preferably from about 40 to about 80 nucleotides long. The polynucleotide may be a linear oligomer of natural or modified monomers and may include deoxyribonucleotides, ribonucleotides and the like that are capable of specifically binding to target polynucleotide by way of monomer to monomer interactions such as through Watson-Crick type base pairing. The skilled artisan will be aware that other molecules capable of base-pairing to nucleic acid targets, such as peptide nucleic acids, are suitable for use in the present invention.

The advantage of employing a ligation reaction, by which a fluorescent labeled oligomer (for example, from 10-mer to 20-mer size) is connected with a non-labeled oligomer, is that the length of a terminal sequence extending from the tagged side of the hairpin (opposite to the part with the attached fluor) to the solid phase can be controlled. In some cases a short distance may be desired for forming stable hybridization using long oligomers as primers. In general, however, it will be appreciated that a long distance is preferred for operation of the invention. Generally, the fluorophore label on the oligomer should be close to the quenching surface when the oligomer is not hybridized with the sample.

Specific hybridization or specific binding between oligonucleotide and complementary nucleic acid as used herein means hybrid formation between an oligonucleotide and a target nucleic acid sequence wherein the oligonucleotide preferentially hybridizes to at least a portion of the target to form a duplex. The polynucleotide or oligonucleotide can be matched perfectly with the target sequence such that the strands making up the duplex form a double stranded structure with one another and every nucleotide in each strand undergoes base pairing with a nucleotide in the other strand. A mismatch, however, may exist within the duplex, provided that the probe and the target remain together long enough during fluorescence readout to permit detection of a signal. A mismatch as termed here means that a pair of nucleotides in the duplex fails to undergo base pairing. The extent of duplex formation can be controlled by altering the stringency of hybridization. The stringency of hybridization is determined by a number of factors during hybridization. Such factors are known and include, among others, temperature, ionic strength, length of time and concentration of formamide. These factors are outlined in, for example, Sambrook et al. (Sambrook et al., *Molecular Cloning A Laboratory Manual* $2^{nd}$ Ed., 1989 Cold Spring Harbor Laboratory Press, Cold Spring Harbor, N.Y. which is incorporated by reference).

A significant disadvantage of earlier approaches to the use of fluorescent-labelled nucleic acid was the requirement for two dyes in close proximity. As a result, it often was necessary to internally label long oligonucleotide probes. In contrast, the present invention involves fluorescence that is generated upon denaturation (loss of base pairing) of one or more probe hairpin structures and is controlled by distance from a large two dimensional quencher. The distances of the present invention can be much larger than those associated with soluble double dye labeled probes.

Accordingly, in the present invention the preferred distance between fluorophore and the surface is determined not only by the fluorescence resonance energy transfer but, also by the polynucleotide lengths required for hybridization. Because of this hybridization and the very large quencher size, the polynucleotide and oligonucleotide lengths that form a duplex are believed to be more important so long as a detectable fluorescence signal can be generated. In one advantageous embodiment, the fluorophore of the oligonucleotide probe should be separated from the surface in the absence of the hairpin structure by at least 20 nucleotides. In another embodiment, the oligonucleotide comprises two (or more than two) hairpins (for example, each greater than 20-mer size) and both hairpin portions hybridize to the targeted nucleic acid, which provides longer separation distances such as 75 Angstroms or more. Thus, probes having multiple hairpin structures also may be used for the invention and are limited only by their effect on the distance between the fluorophore label and the quenching surface, i.e. where the effect of the surface in quenching the fluorescence is a long range effect, probes with multiple hairpin loops may be employed to increase the distance between the fluorophore and the surface.

A nucleic acid sample that is tested according to the methods in this invention can be obtained from virtually any source including virus, bacteria, fungi, plants, invertebrates and vertebrates including humans and other mammals, birds and the like. If only small amounts of a particular target nucleic acid are available in the sample, then amplification by polymerase chain reaction can be used in preparation for the assay (see, for example, Kwok et al., *Genomics* 23:138–144, 1994 which is incorporated by reference). Other amplification methods, such as the ligase chain reaction, can be used.

Test kits that include one or more probes according to the invention are contemplated that can be sold, for example, in packages to aid research, clinical, and testing labs to carry out the invention. Such kits contain as a minimum, at least one fluorophore labeled probe molecule linked to a solid phase, and may include thermostable DNA polymerase, other buffers and reagents needed for the procedure, and instructions for carrying out the assay. Kits can be packaged for manual or automated procedures. All reagents are packaged in containers for storage at freezer, refrigerator, or room temperature.

B. Fluors and Methods for their Attachment

A wide variety of fluors and chemistries for their attachment to nucleic acid are known. The following substances are preferred for the invention; rhodamine type fluorophores such as sulforhodamine 101, phycobilliproteins such as B-phycoerythrin and R-phycoerythrin, fluorescein, 4-nitrobenzo-2-oxa-1,3-diazol, nile blue and their derivatives. When phycobilliprotein is used, it is necessary to couple it using, for example, a biotin-avidin system, in order to ensure thermal stability and stability against a denaturant. Other advantageous fluorophores are known in the art and can be used in the present invention (see for example, Pesce et al., eds, *Fluorescence Spectroscopy*, Marcel Dekker, New York, 1971; White et al., *Fluorescence Analysis: A Practical Approach*, Marcel Dekker, New York, 1970; *Handbook of Fluorescent Probes and Research Chemicals*, $6^{th}$ Ed, Molecular Probes, Inc., Eugene, Oreg., 1996.)

The type of fluorophore to be used is chosen based on a consideration of the fluorescence system (type of excitation light and detector and filters) and background light phenomena. Representative examples of long-wavelength fluors are given in U.S. Pat. Nos. 5,800,995, and 5,571,388. Such long wavelength fluors are particularly useful in combination with a solid state diode laser, which produces coherent light and which does not require a light excitation filter. These long wavelength fluorophores also are contemplated for long distance hairpin(s) because the longer wavelength may provide better optical qualities. More specifically, a "long wavelength" fluorophore has an excitation wavelength greater than 600 nm and may provide a lower background when using with samples derived from biological sources.

The fluorophore can be introduced by various ways; for example, (i) a fluorophore-labeled nucleotide monomer could be introduced by a polymerase or terminal transferase reaction, (ii) the fluorophore-labeled oligonucleotide may be bonded covalently by a ligation reaction, (iii) biotin can be introduced into the DNA and the fluorophore-labeled avidin or the like is bonded to biotin, (iv) chemical reaction of an amine or thiol modified oligonucleotide with an appropriate derivative of the fluorophore, or (v) DNA is made fluorescent by etheno-reaction. All of these methods are known in the art.

C. Quenching Surfaces, Probe Immobilization and Washing

A variety of solid surfaces that quench fluorescence are known to the skilled artisan. Particularly advantageous in this context are surfaces that conduct electricity, such as gold, aluminum, platinum, carbon glass, doped selenium, germanium or silicon, glass or quartz doped with metal such as a transition metal or lanthanide, organic conducting polymer and the like. Also advantageous is a surface coated with a quenching substance such as dye-labelled protein. In this context, a protein that has not been derivatized also may be used because of the presence of residues such as tyrosine and tryptophan in the protein, which can quench the fluorescence.

Solid surfaces also can be modified by adsorption of a small molecule with an absorption spectrum which overlaps the emission spectrum of the reporting fluorophore of the hairpin probe. The small molecule should have a high molar absorptivity to promote efficient quenching of the fluorophore. Examples of a particularly useful small molecule quencher is dabcyl, although others will be known to those skilled in the art. The small molecule quencher can be immobilized on the surface either non-covalently or covalently or in a particularly advantageous embodiment could be incorporated to an oligonucleotide sequence that is coadsorbed with the hairpin-forming probe molecule.

In some embodiments of the invention, the surface is flat and the electrically conductive material exists as a two dimensional sheet. However, in other embodiments, the solid surface may be a sheet having a conductive material deposited thereon in a pattern such as dots or lines. In yet other embodiments, the solid surface is a microparticle in suspension or in a spongy mass, such as a selenium sol particle, gold sol particle or platinum particle. Selenium and gold sol particles are particularly advantageous because of their ease of formation and derivitization with a nucleic acid. The solid surface also may be a gel, for example, a hydrogel. In general, in the context of the present invention, a "solid surface" is a surface that is in a different phase from the solution containing the target molecule, i.e. the surface is one that can bind a probe in such a manner that the probe cannot freely diffuse in solution.

Fluorescence quenching from the fluorophore to the solid phase is dependent upon the distance from the fluorophore to the quencher. In related quenching studies between fluors on the same molecule, it was shown that quenching was near complete for separation distances of about 12 angstroms, whereas about 16% quenching was observed for a separation distance of about 45 angstroms.

The invention specifically contemplates such quenching as described above, in an embodiment where a fluor-quencher is linked to the surface. Example 1 discloses the use of a quencher-labeled protein and avidin-biotin to create a readout system that relies on this intermolecular separation to detect duplex formation.

However, the invention also contemplates using an electrically conductive solid phase to quench fluorescence, wherein the relative distances between the fluorophore and the solid phase that produces quenching is much greater than that seen between individual dye molecules. In fact, separations of fluorophore and solid phase of more than about 120 Angstroms can produce detectable quenching, depending on conditions such as the nature of the solid phase and the wavelength of the fluorophore emission energy. For example, a longer wavelength fluorophore in some cases may allow a longer quenching distance than a short wavelength fluorophore.

Probes can be immobilized to the surface by well known methods, including simple non-covalent absorption driven by free energy changes of the system, and covalent coupling of the nucleic acid to the surface. Particularly advantageous procedures for attachment to silicon dioxide surfaces are based on well-established silicon chemistry (Parkam et al., Biochem. Biophys. Res. Commun., 1:1–6 (1978); Lund et al., Nucl. Acids Res. 16:10861–10880, (1988)). For example, this chemistry may be used to introduce a linker group onto the silicon dioxide (glass) bearing a terminal epoxide moiety that specifically reacts with a terminal primary amine group on the oligonucleotide. This versatile approach (using epoxy silane) is inexpensive and provides a dense array of monolayers that can be readily coupled to terminally modified (amino- or thiol-derivatized) oligonucleotides. The density of probe attachment may be controlled over a wide range by mixing long chain amino alcohols with the amine-derivatized oligonucleotides during attachment to epoxysilanized glass. This strategy essentially produces a monolayer of tethered DNA, interspersed with shorter chain alcohols, resulting in attachment of oligonucleotides down to 50 nm apart on the surface. Variable length spacers may optionally be introduced onto the ends of the oligonucleotides, by incorporation of triethylene glycol phosphoryl units during the chemical synthesis. These variable linker arms are useful for determining how far from the substrate surface oligonucleotide probes should be separated to be readily accessible for pairing with the target DNA strands.

Thiol chemistry, adapted from the method of Whitesides and coworkers on the generation of monolayers on gold surfaces (Lee et al. Pure & Appl. Chem. 63:821–828 (1991) and references cited therein.), may be used for attachment of DNA to gold and platinum surfaces. Dithiols (e.g., 1,10-decanedithiol) are linked at one terminus to the metal surface, and also provide a terminal, reactive thiol moiety for reaction with bromoacetylated oligonucleotides. The density of attachment of DNA to gold or platinum surfaces is controlled at the surface-activation stage by use of defined mixtures of mono- and dithiols.

In a particularly advantageous embodiment, combinatorial synthesis of probes is carried out in situ on the surface of the substrate. Another advantageous approach uses a photolithography process to provide combinatorial synthesis of probes in situ on the surface of the substrate. In this approach, light from a mercury lamp is directed through a photolithographic mask onto the surface of the substrate, cleaving a photoactive group and providing a 5' hydroxy group capable of coupling with another nucleotide. By directing the lamp's light to specific locations on the substrate's surface, the mask determines which nucleotides are activated. Successive rounds of deprotection and coupling reactions efficiently generate oligonucleotides up to 30 bases in length. This strategy has been employed to generate a variety of microarrays. For instance, a set of four arrays containing over 250,000 25-mer oligonucleotides has been made to assay expression of all putative genes in the complete yeast genome sequence. (See Wodica et al. *Nature Biotechnology* 15: 1359–1367 (1997). See also Fodor et al., Science 251: 767–773 (1991); Pirrung et al., WO 90/15070 and Pirrung et al., U.S. Pat. No. 5,143,854 issued Sep. 1, 1992; Cho et al., *PNAS* 95: 3752–3757 (1998); Saizieu et al., *Nature Biotechnology* 16: 45–48 (1998); and Lockhart et al., *Nature Biotechnology* 14: 1675–1996 (1996)). Another in situ approach involves the use of an annular mechanism to deliver reagents to selected areas of a surface in a series of addition reactions. (See Milner et al., *Nature Biotechnology* 15: 537–541 (1997)). The particular overlap of reagent exposures at various locations on the surface defmes the array members.

Figure 4:
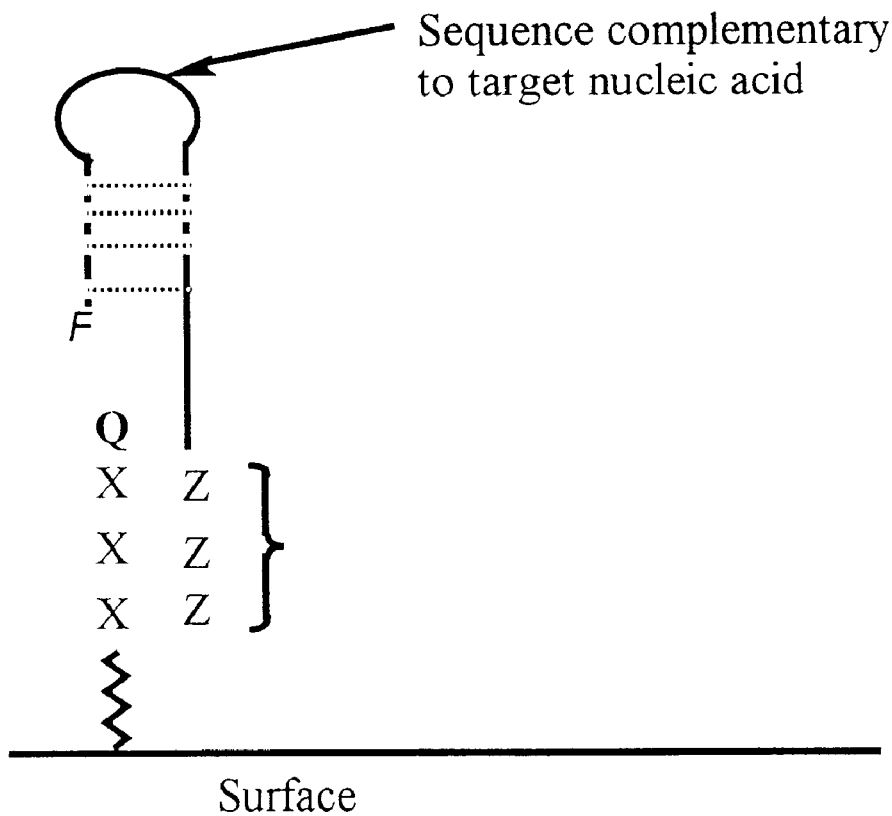
FIG. 4 shows a method of immobilizing an array of probes by base pairing of a region of the probe with a nucleic acid arrayed on a surface. The surface nucleic acid contains a quenching moiety that is maintained in close proximity to the probe fluorophore by the hairpin loop structure of the probe in the absence of target. When the probe binds to target the hairpin dissociates, quenching ceases, and fluorescence increases.

In another embodiment, shown schematically in FIG. 4, an array of probes on a surface is prepared by hybridization to quencher containing nucleic acid molecules on the surface. In this embodiment, the surface is activated with a cross linker, one end of which binds to the surface and the other of which binds to a short nucleic acid (NA) or peptide nucleic acid (PNA) sequence (XXX in FIG. 4). The NA or PNA is terminated by a quenching moiety (Q in the FIG. 4) and is spotted or arrayed on the surface such that each location ('spot') on the surface has a corresponding sequence, i.e. the sequence XXX encodes its location. As each position in the encoding sequence has 4 possible bases a sequence of n bases in the encoding region will define $4^n$ possible locations. For example an encoding sequence of 5 bases would provide for 1024 spots.

A mixture of oligonucleotide probes is then added to the surface. Each nucleotide has the following features:

1. A short sequence of NA or PNA at one end that is complementary to the surface encoding sequence (designated ZZZ in the FIG. 4).
2. A sequence that forms an internal stem loop structure.
3. A region in the loop that is complementary to the target nucleic acid sequence.
4. A fluorescent group at the other end.

The complementary nature of XXX and ZZZ means each probe "finds" its encoded location on the surface and binds there. Subsequent hybridization of the target nucleic acid to the loop region breaks the base pairing in the stem and increases the distance between the fluorophore and quencher so resulting in an increase in fluorescence. The array is reusable by washing with hot water/buffer solution to dissociate both the target and the probe and then re-addition for a mixture of probes which may be either the same or different for the first mixture.

Test devices according to the invention thus comprise at least one discrete surface with an attached probe and more preferably multiple surfaces, where those multiple surfaces advantageously are individual dots, lines or other geometric arrangements of immobilized probes within or on a plane. Particularly advantageously, the immobilized probe surfaces can be washed after their use, to allow reuse of the same surface for testing further samples. In this case, it is desirable to immerse the surface(s) in a chaotropic solution or detergent, and to control temperature and salt concentration to remove bound material and also to re-form hairpin structures of the probe.

In a particularly advantageous embodiment, a surface may be recalibrated prior or during its reuse by measuring its intrinsic fluorescence. Thus, as a probe surface is reused, the level of intrinsic fluorescence may increase. In the present invention, the level of intrinsic fluorescence can be measured and subtracted from the measured fluorescence levels during contact with a test sample.

In another advantageous embodiment of a surface having multiple bound probes, a reference nucleic acid is added at a known concentration to the test sample. The reference nucleic acid binds to one of the immobilized probe sites, allowing an internal real-time control to monitor the state of the device surface and correct for device deterioration, as well as monitor the hybridization reaction time.

D. Two-Dimensional Arrays of Probes

One particularly advantageous embodiment of the invention comprises a microfabricated apparatus having separate areas for immobilizing various nucleic acid probes. Known microfabricated binding devices such as those described in U.S. Pat. No. 5,843,767 typically are rectangular wafer-type apparatuses with a surface area of approximately one $cm^2$, e.g., 1 cm×1 cm. The bounded regions on such devices are typically present in a density of 100–10000 regions/$cm^2$, although the apparatus can be constructed with much higher densities.

A microfabricated apparatus as described herein is useful not only for nucleic acid sequence analysis by hybridization, but also for analysis of patterns of gene expression by hybridization of cellular mRNA to an array of gene-specific probes and even to detect other non-hybridizing biochemical reactions such as, immunochemical analysis of protein mixtures, epitope mapping, assay of receptor-ligand interactions, and profiling of cellular populations involving binding of cell surface molecules to specific ligands or receptors immobilized within individual binding sites. These other biochemical reactions are detected, according to an embodiment of the invention, by sterically coupling the biochemical reaction with self-hybridization of the hairpin of the probe. For example, an antigen can be covalently coupled to the probe near the middle of the hairpin forming area. This coupling can be achieved using methods that are known in the art. Upon incubation with an antibody that recognizes the antigen, an antigen-antibody complex is formed, which interferes with correct hybridization, causing the fluorophore to move away from the surface. In this embodiment, the probe is used to detect a binding reaction that takes place between a ligand on the probe, and a target ligand in a test solution. Although nucleic acid analysis is one principal use for such an microapparatus the nucleic acid duplex formed can be applied to a broad range of molecular binding reactions involving small molecules, macromolecules, particles, and cellular systems. See, for example, the uses described in WO 89/10977.

Ordinarily a microfabricated apparatus that contains a probe(s) according to the invention can discriminate between regions in which binding has taken place and can quantitate the relative extent of binding in different bounded regions by detecting a change in fluorescence. A highly preferred method of detection in this regard is a charge-coupled-device array or CCD array. With the CCD array, an individual pixel or group of pixels within the CCD array is placed adjacent to or focused upon each confmed region of the substrate where detection is desired. A fluorescence increase at a test site is used to determine where hybridization has taken place.

The present invention also is applicable to DNA chip technology wherein a particular marker polynucleotide is at a particular address site on the chip (See Pease et al., *Proc. Natl. Acad. Sci.* 91:5022–6, 1995 which is incorporated by reference). Pease describes a chip to which molecules are attached and in which a voltage is applied selectively to one or more areas to turn on or turn off the detection system at selected portion(s). This chip design is particularly useful and contemplated for use with probes of the present invention. Turning on a voltage to an area having an attached probe will, depending on the voltage, disable the detection system and, in some instances, even enhance operation of the system. The actual voltages used in this context may be determined by routine optimization as is known in this art.

In a particular advantageous embodiment the solid surface is in a flow-through porous form wherein probe molecules are tethered throughout a large surface area. Suitable surfaces are described in U.S. Pat. No. 5,843,767, which is hereby incorporated by reference. Optionally, the surface has localized discrete and isolated sites for binding reactions. In another embodiment microfabricated devices are constructed that further include at least one microelectronic component in each test site, permitting rapid, addressable detection of hybridization across the array. A microelectronic component may be a spot of electrically conductive material such as aluminum that is electrically attached to a circuit and which can accept an electrostatic charge by virtue of application of a voltage to the spot from the circuit. In one embodiment the component is an electrically conductive dot or other geometric shape to which the probe is attached directly. Preferably, the component also may be electrically coupled by its back side to a circuit that imposes a voltage upon the component to turn on, turn off or otherwise modulate activity of the probe.

According to this embodiment of the invention, individual species of probes are immobilized within densely packed pores or channels, arranged in patches across a wafer of solid support material. Known microfabrication techniques are available to produce microchannel or nanochannel glass and porous silicon useful as support wafers. Such flow-through devices, as conceived here can utilize a variety of conventional detection methods, including microfabricated optical and electronic detection components, film, charge-coupled-device arrays, camera systems and phosphor storage technology, to separately detect and or resolve a fluorescence signal for each species of probe.

The invention is particularly useful in embodiments having multiple probe species immobilized in multiple microchannels and provides the following advantages over flat surface designs:

(1) improved detection sensitivity due to the vastly increased surface area which increases the quantity of probe bound per cross sectional area;

(2) minimization of a rate-limiting diffusion step preceding the hybridization reaction (reducing the time required for the average target molecule to encounter a surface-tethered probe from minutes to milliseconds), speeding hybridization and enabling mismatch discrimination at both forward and reverse reactions;

(3) enablement of the analysis of dilute nucleic acid solutions because of the ability to gradually flow the solution through the porous wafer;

(4) facilitation of subsequent rounds of hybridization involving delivery of probes to specific sites within the hybridization array; and (5) facilitation of the chemical bonding of probe molecules to the surface within each isolated region due to the avoidance of the rapid drying of small droplets of probe solution on flat surfaces exposed to the atmosphere.

Accordingly, the present invention contemplates probes, apparatus and method for the simultaneous conduct of a multiplicity binding reactions on a substrate, which substrate is a microfabricated device comprising a set of discrete and isolated regions on the substrate, such that each such discrete and isolated region corresponds to the location of one such binding reaction. Descriptions of substrates contemplated in this context are found in for example, U.S. Pat. Nos. 5,843,767 and 5,741,644. Some of the substrates described in the art are non-conducting glass, and it is readily appreciated that the surfaces of such substrates can be given fluorescence quenching properties by doping the solid phase material (typically glass or silicon) with suitable ion(s), or by coating the surface with a suitable quencher such as a dye-labelled protein, for example, fluorescein-labeled serum albumin. Other representative reactions to carry out the embodiment of 2-dimensional testing are known to the skilled artisan as exemplified by the description of Strezoska et al, *Proc. Natl. Acad. Sci. USA*, Vol. 88, PP. 10089–10093 (1991)).

E. Use of Immobilized Probes in Plasmon Wave and Electron Transfer Devices

Devices and surfaces described for surface plasmon resonance to detect nucleic acid hybridization are particularly useful with the probes and methods of the invention. Surface plasmon resonance is the oscillation of the plasma of free electrons which exists at a metal boundary. These oscillations can be detected to determine a change in the refractive index of a material adjacent to the metal surface. DNA duplexes formed between a probe and a target sequence according to the invention form in the material adjacent to the metal surfaces and can be detected. Plasmon wave optics are particularly useful for practice of the invention because they provide a light beam that can be totally internally reflected at the boundary of the medium used (such as glass) and this is may be used as a light source for exciting a fluor-labeled probe according to the invention. When using such a device it is important to select conditions such that the emitted fluorescent light is at a different wavelength and can be detected from the sensor (i.e. not internally reflected).

In one embodiment, polarized excitation light is internally reflected, and non-polarized fluorescence light, or differently polarized light is detected. This embodiment decreases background light measurement, for better sensitivity because bound probe will absorb and emit light that is polarized in the plane of the fluorophore which is held, preferably in a perpendicular orientation with respect to the plane of the solid surface. Upon binding with sample, a fluorophore becomes free and can absorb light outside of that plane.

A skilled artisan in the field of surface plasmon resonance sensors will readily appreciate variations in how to use a probe according to the invention. Basically, a detector should comprise: (1) a source of light matched in wavelength with the fluorophore absorption spectrum; (2) a block of transparent material such as glass on one surface of which is applied a thin film of metal, for example silver or gold, and on which is supported a test medium such that the metal film is sandwiched between the medium and the glass block; (3) a means for directing the light into the transparent block, preferably to allow total internal reflection of the radiation at the surface of the block to which the metal film is applied; and (4) a light detector, preferably with an emission filter matched to the emission wavelength profile of the fluorophore.

The detector preferably is a photon multiplier in the photon counting mode and a fluorophore is chosen that has a wavelength suitable for monitoring a difference in quenching upon formation or dissolution of the hairpin structure of the probe, as described above. In practice, a fluorophore is chosen having an excitation wavelength that matches the optimum wavelength needed for total or near total internal reflection and thus optimum excitation of the fluor, while the emission wavelength and/or polarization differs as needed to allow emission light to escape the device and be detected. In one embodiment, the excitation light and the emission light share the same transparent block and the fluorophore Stokes shift, along with suitable emission and excitation filters, is used to keep the photomultiplier from overload. In another embodiment, the emission light path to the photodetector from the transparent block is perpendicular with respect to the excitation light path, in order to keep excess light from the photodetector.

A plasmon resonance sensor modified for fluorescence detection as described above can be used according to the invention for multiple simultaneous assays with different oligomeric nucleic acids in a two dimensional array. This embodiment of the invention is particularly suited for multiple probe detection of individual bands simultaneously from electrophoretically separated nucleic acid samples. An apparatus for making a sensor that can be adapted for this use with an electrophoresis gel is described in U.S. Pat. No. 5,035,863. That patent discloses a two dimensional surface comprising a discontinuous multi-dot metal film in contact with an electrophoresis gel surface and that simultaneously monitors a plurality of tracks through the gel. In one embodiment according to the claimed invention, a discontinuous metal layer as described in that patent is combined with probes as described herein. The probes are attached to the metal spots on the two dimensional flat surface in contact with an electrophoresis gel surface and smaller areas of the flat surface are scanned by an excitation light beam.

In one embodiment, the solid phase is silver or gold and is applied by evaporation. In another embodiment, the solid phase is a semiconductor that is doped to form an N type or P type material that can conduct electrons and which can quench fluorescence. In yet another embodiment, the semiconductor is separated into functional regions that are individually controlled by the application of a voltage. Application of a voltage can modulate the surface properties and can affect quenching. This allows further control for multiple measurements from one sample.

The probes and methods of the invention are particularly useful in combination with surfaces and devices that are designed for nucleic acid mediated electron transfer. Representative examples in this context are provided in U.S. Pat. No. 5,824,473, issued Oct. 20, 1998. For example, poly (vinylpyridine) complex of Os(bpy)2Cl can be cross-linked with an epoxide such as diepoxide to form a redox-conducting epoxide cement which is capable of strongly binding to electrodes made of conductive material such as gold, vitreous carbon, graphite, or another material. The epoxide cross-linked polymer then is reacted with, for example, an exposed amine, such as the amine of an amino-modified nucleic acid, the nucleic acid is attached covalently to the complex, and forms a hydrogel on the surface of the electrode. In another embodiment of the invention, a nucleic acid is linked to a thin film oxidized surface such as a $SnO_2$, $TiO_2$, $RuO_2$ or Pt electrode, as described by Lenhard, and Murray, R. J. *Electroanal. Chem.* 78: 195 (1977). In another embodiment, a fluorophore is chosen that can participate in electron transfer. In this case, a probe according to the present invention is used on a surface that is known to work in electron transfer and is attached under conditions where the probe is close enough to the surface for electron transfer and for fluorescence quenching, but fluorescence detection is used instead of amperometric or voltometric detection.

In another embodiment of the invention, the fluorescent label of the immobilized nucleic acid loses energy by conversion of this energy into a plasmon wave on the solid phase when the fluorophore is near the surface. In particularly advantageous embodiments, total internal reflectance is used to optimize excitation of the fluorophore.

The following examples are provided to illustrate an embodiment of the invention and are not intended to limit the specification or scope of the claims in any way.

EXAMPLE 1

An oligonucleotide probe forming an internal hairpin structure is synthesized with a biotin derivative at one terminus and a fluorescein dye at the other terminus. Streptavidin is immobilized onto a platinum surface through non-covalent (adsorption) forces. The oligonucleotide probe is added and allowed to bind non-covalently to the immobilized streptavidin via the biotin derivative. Upon binding, the fluorescence of the fluorescein dye is quenched by the surface.

A solution of target nucleic acid that contains a sequence complementary to a sequence in the hairpin loop of the probe is added to the prepared surface. Upon incubation the hairpin loop dissociates, moving the dye from the proximity of the surface. The quenching of the fluorescein fluorescence thus is relieved and the intensity of the fluorescence signal increases.

EXAMPLE 2

The procedure described in Example 1 is followed except that a polystyrene surface is used instead of a platinum surface to immobilize the streptavidin and biotin linked oligonucleotide probe.

A solution of target nucleic acid that contains a sequence complementary to a sequence in the hairpin loop of the probe is added to the prepared surface. Upon incubation the hairpin loop dissociates, moving the dye from the proximity of the surface. The quenching of the fluorescein fluorescence thus is relieved and the intensity of the fluorescence signal increases.

EXAMPLE 3

The procedure described in Example 1 is followed except that streptavidin is covalently immobilized to an organosilane modified glass or silicon flow-through porous form. Individual oligonucleotide probes, comprising a biotin derivative at one terminus and a fluorescein dye at the other terminus, are deposited in a spatially arranged array on the flow through porous form. Individual spots are roughly 100 $\mu$m in a diameter and are spaced in a rectangular arrangement with 400 $\mu$m center-to-center spacing. The oligonucleotides bind non-covalently via the biotin derivative to the immobilized streptavidin. Upon binding, with the hairpin structure intact, the fluorescence of the fluorescein dye is quenched due to the close proximity to the surface.

A solution mixture of target nucleic acids is incubated by flowing the mixture through the flow through porous form. When a target nucleic acid complementary to an individual probe sequence is present the duplex is formed, reducing the quenching of the fluorescein, and the intensity of the fluorescence signal increases.

EXAMPLE 4

Avidin Induced Quenching of a Fluorescent DNA Molecule in Solution.

A single stranded synthetic oligonucleotide having the following sequence (SEQ ID NO:1) was prepared ('probe DNA'):

5' <u>GCGAGC</u>TAGGAAACACCAAAGATGATATTT<u>GCTCGC</u> 3'

The underlined sequences are self complementary, allowing formation of a hair pinstructure under appropriate conditions.

At the 5' end a fluorescein group was attached covalently via a six carbon atom long alkyl chain. At the 3' end a biotin group was attached covalently via either a seven or twelve carbon atom long alkyl chain.

A solution of the modified DNA at a concentration of 100 nM (in 100 mM MOPS buffer, pH 7 or a 100 mM carbonate buffer pH 9) was placed in a cuvette in a Perkin Elmer LS50B spectrofluorimeter. The solution was excited with light of wavelength 488 nm. The resulting fluorescence emission intensity was measured at a wavelength of 520 nm.

The modified DNA showed a fluorescence intensity of 125 and upon addition of avidin to a final concentration of 400 nM this was decreased to 65 consistent with the avidin acting to quench the fluorescein fluorescence by virtue of its proximity through binding to the biotin moiety. Addition of DNA with the following sequence (SEQ ID NO:2) ('target DNA'):

5' AAAGAAAAAATATCATCTTTGGTGTTTCCTATTTCCTA 3' at a concentration of 180 nM resulted in an increase in fluorescence to a value of 78.

EXAMPLE 5

Fluorescence Quenching by Streptavidin Coated Magnetic Beads

Commercially available streptavidin coated magnetic beads (Sigma Chemical Corp.) were suspended in a solution (100 mM carbonate buffer pH 9) of 180 nM DNA probe with the sequence shown in Example 4. The beads were magnetically separated from the solution and resuspended in the same buffer and the fluorescence emission intensity measured as described in Example 4 and found to have a value of 13. Next, target DNA was added to a final concentration of 200 nM and the fluorescence remeasured and found to have a value of 26.

EXAMPLE 6

Coating of Flow Thru Chip with Avidin and DNA Probe

1. Chip Cleaning and Silanisation

Several Flow thru chips (each 1.2 cm square) were washed in an ultrasonic bath first with nitric acid (1M) for 15 minutes and then with water for 15 minutes and then with ethanol for 15 minutes. They then were heated at 80° C. in an oven for 1 hour. They were then placed vertically in a vacuum oven. 4 ml of trimethoxythiopropylsilane was placed in a beaker in the oven and a vacuum of 0.1 atmosphere applied for 16 hours at 80° C.

After thoroughly washing with dry toluene and ethanol the chips were stored in methanol at 4° C.

2. Avidin Coating

The chips were immersed in a solution of 2 mM N-[γ-maleimidobutyryloxy]succinimide ester in ethanol for 1 hour. The chip was rinsed and then immersed in a solution of avidin (3 mg/ml in 100 mM MOPS pH 7) for 1 hour at room temperature and fmally washed extensively with 6×SSC.

3. Probe Binding

The chips then were immersed for 1 h in 10×Denhardt's solution diluted in 6×SSC. Finally the probe (100 nM) was dissolved in 6×SSC and added to the chip and incubated overnight.

EXAMPLE 7

Effect of Sodium Ion Concentration on the Fluorescence of a DNA Probe Bound to Avidin on the Surface of a Flow Through Chip An avidin DNA probe coated chip was prepared as described in Example 5 and incubated for 12 hours in a low sodium buffer (100 mM MOPS pH7) where the probe should not be self annealed. Imaging the chip under a fluorescence microscope with a fluorescein filter set gave an intensity of 150 compared to a background (no DNA probe) of 50. Washing the chip under conditions of high sodium ion concentration (100 mM MOPS pH 7+1M sodium chloride) changed the intensity to 55. This decrease (from 100 to 5 after subtracting the background) is consistent with the probe forming an annealed structure that is quenched by the avidin.

EXAMPLE 8

Hybridization to Complementary DNA Sequences Under Diffusive Transport

Chips were prepared with avidin and modified DNA probe as described in Example 6. The intensity when imaged using a fluorescence microscope was 2 (after background subtraction). Addition of a solution of 200 nM target DNA with the sequence shown in Example 4 and incubation overnight increased the fluorescence to a value of 6 (after background subtraction).

EXAMPLE 9

Hybridization to Complementary DNA Sequences Under Convective Transport

8 Chips were prepared as described in Example 6. When imaged as described in Example 6 and after subtraction of the background the mean intensity of the chips was 5 (CV 3%). A solution of 200 nM target DNA (with the sequence shown in Example 3) increased the fluorescence intensity to 6.5 (after background subtraction) in 20 minutes at a recycling flow rate of 750 μl/minute.

The invention has been disclosed broadly and illustrated in reference to representative embodiments described above. Those skilled in the art will recognize that various modifications can be made to the present invention without departing from the spirit and scope thereof. Each publication and each application cited in this disclosure is specifically incorporated by reference in its entirety.

We claim:

1. A method for detecting the presence of a nucleic acid in a test sample, comprising:
   (a) providing a solid phase having an oligonucleotide bound thereon wherein the oligonucleotide comprises a fluorophore, the fluorophore being covalently attached to one end of the oligonucleotide and the solid phase being linked to the opposite end of the oligonucleotide, the oligonucleotide further comprising at least one hairpin structure between the two ends;
   (b) incubating the test sample with the solid phase under conditions suitable for complementary binding between the oligonucleotide and nucleic acid from the test sample; and
   (c) detecting the presence of the nucleic acid in the test sample by detecting fluorescence from the fluorophore.

2. A method as described in claim 1, wherein the solid phase comprises a material selected from the group consisting of: an electrically conductive polymer; a non-electrically conductive polymer; a fluorophore labeled protein; a metal; a metal sheet; a metal particle; gold sol; selenium sol; gold plate; platinum plate; doped semiconducting silicon, germanium or selenium; aluminum; silver; platinum; carbon glass; glass or quartz doped with metal ion; glass or quartz doped with a transitional metal ion; iron oxide; chromium oxide; and glass or quartz doped with a lanthanide.

3. A method as described in claim 1, wherein step C is carried out by excitation of the fluorophore with excitation light in an apparatus wherein the apparatus provides either total internal reflection of the excitation light or direct excitation.

4. A method as described in claim 1, further comprising a calibration step of detecting fluorescence from the fluorophore at a defined temperature prior to step (b).

5. A method according to claim 1, wherein said oligonucleotide is directly covalently bound to said solid phase.

6. A method according to claim 1, wherein said oligonucleotide is indirectly linked to said solid phase.

7. A method as described in claim 2, wherein the solid phase further comprises a surface coating of polymer with covalently attached quenching groups.

8. A method according to claim 6, wherein said solid phase further comprises a nucleic acid comprising a quenching moiety.

9. A method as described in claim 7, wherein the polymer is a protein.

10. A method according to claim 8, wherein said oligonucleotide is indirectly linked to said solid phase by hybridization with said nucleic acid.

11. A method according to claim 8, wherein said solid phase comprises an array of discrete regions wherein each region contains a nucleic acid comprising a quenching moiety.

12. A method according to claim 11, wherein said array comprises a plurality of different nucleic acids.

13. A method for detecting the presence of two or more nucleic acids in a test sample, comprising:
   (a) providing a solid phase having two or more oligonucleotides bound thereon at separate regions wherein each oligonucleotide comprises a fluorophore, the fluorophore being covalently attached to one end of the oligonucleotide and the solid phase being linked to the opposite end of the oligonucleotide, each oligonucleotide further comprising at least one hairpin structure between the two ends;
   (b) incubating the test sample with the solid phase under conditions suitable for complementary binding between the oligonucleotides and nucleic acid from the test sample; and
   (c) detecting the presence of the nucleic acids in the test sample by detecting fluorescence from each of the separate regions of the solid phase.

14. A method as described in claim 13, wherein the solid phase comprises a material selected from the group consisting of: an electrically conductive polymer; a non-electrically conductive polymer; a fluorophore labeled protein; a metal; a metal sheet; a metal particle; gold sol; selenium sol; gold plate; platinum plate; doped semiconducting silicon, germanium or selenium; aluminum; silver; platinum; carbon glass; glass or quartz doped with metal ion; glass or quartz doped with a transitional metal ion; iron oxide; chromium oxide; and glass or quartz doped with a lanthanide.

15. A method as described in claim 13, further comprising a calibration step of detecting fluorescence from at least one region at a defined temperature prior to step (b).

16. A method as described in claim 13, further comprising a signal selection step of applying an electric charge to part of the solid phase prior to step (c).

17. An analytical test device for detecting the presence of a nucleic acid in a test sample comprising:
- a solid phase surface comprising a material that quenches fluorescence; and
- a self-complementary single stranded oligonucleotide probe linked to the solid phase surface at one of its ends, the probe comprising a fluorophore attached to its other end and a hairpin structure between the two ends.

18. A test device as described in claim 17, wherein the material that quenches fluorescence comprises a substance selected from the group consisting of: an electrically conductive polymer; a non-electrically conductive polymer; a fluorophore labeled protein; a metal; a metal sheet; a metal particle; gold sol; selenium sol; gold plate; platinum plate; doped semiconducting silicon, germanium or selenium; aluminum; silver; platinum; carbon glass; glass or quartz doped with metal ion; glass or quartz doped with a transitional metal ion; iron oxide; chromium oxide; and glass or quartz doped with a lanthanide.

19. An analytical test device for detecting the presence of two or more nucleic acids in a test sample comprising:
- a solid phase surface comprising a material that quenches fluorescence and having two or more oligonucleotides bound thereon at separate regions wherein each oligonucleotide comprises a fluorophore, the fluorophore being covalently attached to one end of the oligonucleotide and the solid phase being linked to the opposite end of the oligonucleotide, and wherein each oligonucleotide further comprises a hairpin structure between the two ends.

20. A test device as described in claim 19, wherein the material that quenches fluorescence comprises a substance selected from the group consisting of: an electrically conductive polymer; a non-electrically conductive polymer; a fluorophore labeled protein; a metal; a metal sheet; a metal particle; gold sol; selenium sol; gold plate; platinum plate; doped semiconducting silicon, germanium or selenium; aluminum; silver; platinum; carbon glass; glass or quartz doped with metal ion; glass or quartz doped with a transitional metal ion; iron oxide; chromium oxide; and glass or quartz doped with a lanthanide.

21. A test device as described in claim 19, wherein the solid phase surface is in a flow-through porous form.

22. A test device as described in claim 19, further comprising at least one microelectronic component at each of the separate regions to permit addressable detection of hybridization.

23. A test device as described in claim 19, wherein the solid phase surface is a discontinuous multi-dot metal film in contact with an electrophoresis gel surface.

24. A test device as described in claim 22, wherein each microelectronic component comprises the separate region of the solid phase surface that has an oligonucleotide bound thereon.

25. A test device as described in claim 24, wherein the microelectronic component at each of the separate regions can apply a voltage for addressable detection of hybridization.

26. A kit for detecting the presence of a nucleic acid in a test sample, comprising:
- a solid phase having an oligonucleotide bound thereon wherein the oligonucleotide comprises a fluorophore, the fluorophore being covalently attached to one end of the oligonucleotide and the solid phase being linked to the opposite end of the oligonucleotide, the oligonucleotide further comprising a hairpin structure between the two ends packaged in a container; and instructions.

27. A fluorescence quenching surface having at least one type of oligonucleotide bound thereon wherein the oligonucleotide comprises a fluorophore, the fluorophore being covalently attached to one end of the oligonucleotide and the solid phase being linked to the opposite end of the oligonucleotide, the oligonucleotide further comprising at least one hairpin structure between the two ends.

28. A fluorescence quenching surface as described in claim 27, wherein the surface is in the form of a flat surface upon which multiple oligonucleotide types are bound at discrete positions.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Unknown
<220> FEATURE:
<221> NAME/KEY: misc_feature
<222> LOCATION: ()..()
<223> OTHER INFORMATION: probe DNA

<400> SEQUENCE: 1
gcgagctagg aaacaccaaa gatgatattt gctcgc                    36

<210> SEQ ID NO 2
<211> LENGTH: 38
<212> TYPE: DNA
<213> ORGANISM: Unknown
<220> FEATURE:
<221> NAME/KEY: misc_feature
<222> LOCATION: ()..()
<223> OTHER INFORMATION: target DNA

<400> SEQUENCE: 2
aaagaaaaaa tatcatcttt ggtgtttcct atttccta                  38